(12) United States Patent
Sun et al.

(10) Patent No.: US 10,618,868 B2
(45) Date of Patent: Apr. 14, 2020

(54) METHOD FOR PREPARING 2-ARYL MALONAMIDE AND APPLICATIONS THEREOF

(71) Applicant: ORIENTAL(LUZHOU) AGROCHEMICALS. CO., LTD., Luzhou, Sichuan (CN)

(72) Inventors: Yinwei Sun, Zhejiang (CN); Zhongyuan Wang, Zhejiang (CN); Yanyan Huang, Zhejiang (CN); Bangchi Chen, Zhejiang (CN)

(73) Assignee: ORIENTAL(LUZHOU) AGROCHEMICALS. CO., LTD., Luzhou (CN)

( * ) Notice: Subject to any disclaimer, the term of this patent is extended or adjusted under 35 U.S.C. 154(b) by 0 days.

(21) Appl. No.: 16/585,850

(22) Filed: Sep. 27, 2019

(65) Prior Publication Data
US 2020/0024220 A1    Jan. 23, 2020

Related U.S. Application Data

(63) Continuation of application No. PCT/CN2017/079686, filed on Apr. 7, 2017.

(51) Int. Cl.
*C07C 231/06* (2006.01)
*C07C 233/11* (2006.01)
*C07D 498/04* (2006.01)

(52) U.S. Cl.
CPC ......... *C07C 231/06* (2013.01); *C07C 233/11* (2013.01); *C07D 498/04* (2013.01)

(58) Field of Classification Search
None
See application file for complete search history.

(56) References Cited

FOREIGN PATENT DOCUMENTS

| CN | 1355806 A | 6/2002 |
|---|---|---|
| WO | 0078712 A1 | 12/2000 |
| WO | 0078881 A2 | 12/2000 |
| WO | 2004050607 A1 | 6/2004 |

OTHER PUBLICATIONS

Chen Lipeng et al. The Synthesis of 2-(2,6-Diethyl-4-methylphenyl) malonamide. Agrochemicals, 2014, 53(8): 558-560.
Masahiro Yokoyama et al. Realization of the synthesis of a,a-disubstituted carbamylacetates and cyanoacetates by either enzymatic or chemical functional group transformation, depending upon the substrate specificity of Rhodococcus amidase. Tetrahedron:asymmetry. Sep. 20, 2014, 15(18), pp. 2817-2820.

*Primary Examiner* — Sudhakar Katakam
*Assistant Examiner* — Jennifer C Sawyer
(74) *Attorney, Agent, or Firm* — Wayne & Ken, LLC; Tony Hom

(57) ABSTRACT

Disclosed are a method for preparing 2-aryl malonamide and an application thereof. This method uses 2-(cyclohexenylidene) malononitrile as a raw material, which undergoes an aromatization-hydrolyzation reaction in the presence of an oxidant and water to produce 2-aryl malonamide by one step. Compared to the prior art, the method for preparing 2-aryl malonamide of this application has the following features and advantages: (1) this method employs a completely different synthetic strategy; (2) raw materials used in this method are easily obtained; (3) this method not only has high yield, but also does not require expensive metal catalysts. This method is lower-cost, suitable for the industrial production.

10 Claims, No Drawings

METHOD FOR PREPARING 2-ARYL MALONAMIDE AND APPLICATIONS THEREOF

CROSS-REFERENCE TO RELATED APPLICATIONS

This application is a continuation of International Patent Application No. PCT/CN2017/079686, filed on Apr. 7, 2017, which is incorporated herein by reference in its entirety.

TECHNICAL FIELD

This application relates to organic synthesis, and specifically to a method for preparing 2-aryl malonamide and applications thereof.

BACKGROUND 2-aryl malonamide compounds are a class of intermediates in the organic synthesis, for example, 2-(2,6-diethyl-4-methylphenyl) malonamide is an important intermediate in the preparation of a highly-effective herbicide Pinoxaden (WO 00/78881, WO 00/78712).

Currently, the 2-aryl malonamide compounds are mainly prepared through the hydrolyzation of 2-aryl malononitrile compounds (WO 00/78712). However, this method has the defect of difficulty in preparing the 2-aryl malononitrile compounds, especially the more sterically-hindered 2-(2,6-disubstituted aryl) malononitrile. The most effective method of synthesizing 2-(2,6-disubstituted aryl) malononitrile is to use the corresponding aromatic amine as a raw material, which sequentially undergoes diazotization-halogenation (Sandmeyer) reaction and metal-catalyzed C—C coupling reaction to form the 2-(2,6-disubstituted aryl) malononitrile (WO 2004/050607). However, in order to achieve an ideal yield of the metal-catalyzed coupling reaction, an expensive bromine or iodine compound is required to be used as a halogenating agent in the diazotization-halogenation reaction. The diazotization-halogenation reaction will produce large amount of waste pollution, and also leads to safety and halogen corrosion problems. Moreover, the organometallic catalyst used in the metal-catalyzed C—C coupling reaction between the sterically-hindered aryl halide and the malonic acid derivative is expensive and difficult to be recycled.

The inventors of the present invention, through continuous research and exploration, have surprisingly developed a method for preparing 2-aryl malonamide compounds directly from raw materials of 2-(cyclohexenylidene) malononitrile.

SUMMARY

This application provides a novel method for preparing 2-aryl malonamide compounds. Specifically, this method comprises: subjecting 2-(cyclohexenylidene) malononitrile 1 to an aromatization-hydrolyzation reaction in the presence of an oxidant and water to produce 2-aryl malonamide 2 by one step; as shown in the following reaction scheme:

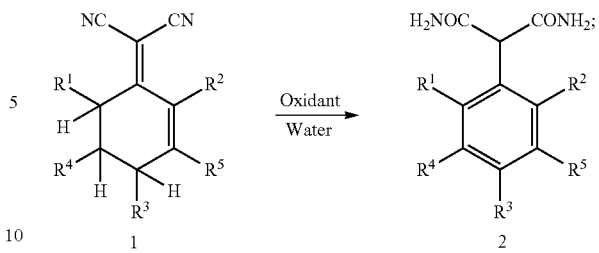

wherein $R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur.

The oxidant is a peroxide, oxygen, air or an oxidizing acid, preferably hydrogen peroxide, potassium persulfate or concentrated sulfuric acid. A molar ratio of the oxidant to the compound 1 is 0.5-2.0:1, preferably 1.0-1.2:1.

A temperature of the aromatization-hydrolyzation reaction is 0-100° C., preferably 60-80° C.

The aromatization-hydrolyzation reaction is performed in the presence of an acid. Preferably, the acid is concentrated sulfuric acid.

Compared to the prior art, the method for preparing 2-aryl malonamide of this application has the following features and advantages.

(1) This method employs a completely different synthetic strategy.

(2) Raw materials used in this method are easily obtained.

(3) This method not only has high yield, but also does not require expensive metal catalysts. This method is lower-cost, suitable for the industrial production.

DETAILED DESCRIPTION OF EMBODIMENTS

Some features of this application will be further illustrated below with reference to the embodiments, but these embodiments are not intended to limit this application.

The raw materials used in the invention can be prepared by Knoevenagel condensation of cyclohexenone and malononitrile (*J. Mol. Cata. A. Chem.* 2003, 195 (1-2), 263).

Example 1 Preparation of 2-(2,6-diethyl-4-methylphenyl) malonamide 43.0 g of 2-(2,6-diethyl-4-methyl-2-ene-1-cyclohexylidene) malononitrile (0.20 mol), 54.1 g of potassium persulfate (0.2 mol) and 5.4 g of water (0.30 mol) were cooled to 0-5° C. Concentrated sulfuric acid was dropwise added to the reaction mixture which was then heated to 70° C. for reaction. After the reaction was completed, the reaction mixture was cooled, poured into ice water and extracted twice with ethyl acetate. The organic phases were combined, dried and crystallized by concentration to give 40.0 g of 2-(2,6-diethyl-4-methylphenyl) malonamide, and the yield was 80%.

$^1$H NMR (MeOD, 500 MHz): δ 6.99 (s, 2H), 4.81 (s, 1H), 2.60 (q, J=9.0 Hz, 4H), 2.32 (s, 3H), 1.22 (t, J=9.0 Hz, 6H).

NMR (CDCl$_3$, 125 MHz): δ 174.7, 145.0, 139.0, 130.2, 128.9, 48.9, 27.5, 21.2, 15.5.

Example 2 Preparation of 2-(2,6-diethyl-4-methylphenyl) malonamide 21.4 g of 2-(2,6-diethyl-4-methyl-2-ene-1-cyclohexylidene) malononitrile (0.10 mol) and 13.6 g of 30% hydrogen peroxide (0.12 mol) were cooled to 0-5° C. The reaction mixture was heated to 60° C. for reaction. After the reaction was completed, the reaction mixture was cooled, poured into ice water and extracted twice with ethyl acetate. The organic phases were combined, dried and crystallized by concentration to give 10.2 g of 2-(2,6-diethyl-4-methylphenyl) malonamide.

Example 3 Preparation of 2-(2,6-diethyl-4-methylphenyl) malonamide 32.1 g of 2-(2,6-diethyl-4-methyl-2-ene-1-cyclohexylidene) malononitrile (0.15 mol) and 6.7 g of water (0.30 mol) were cooled to 0-5° C. Concentrated sulfuric acid was dropwise added to the reaction mixture which was then heated to 80° C. for reaction. After the reaction was completed, the reaction mixture was cooled, poured into ice water and extracted twice with ethyl acetate. The organic phases were combined, dried and crystallized by concentration to give 32.7 g of 2-(2,6-diethyl-4-methylphenyl) malonamide, and the yield was 88%.

Example 4 Preparation of 2-(2,6-diethyl-4-methylphenyl) malonamide 214.3 g of 2-(2,6-diethyl-4-methyl-2-ene-1-cyclohexylidene) malononitrile (1.00 mol) and 27.0 g of water (1.50 mol) were cooled to 0-5° C. The reaction mixture was dropwise added with concentrated sulfuric acid and simultaneously introduced with oxygen. The reaction mixture was then heated to 80° C. for reaction. After the reaction was completed, the reaction mixture was cooled, poured into ice water and extracted twice with ethyl acetate. The organic phases were combined, dried and crystallized by concentration to give 136.6 g of 2-(2,6-diethyl-4-methylphenyl) malonamide.

Example 5 Preparation of 2-(3-methylphenyl) malonamide 15.0 g of 2-(3-methyl-2-ene-1-cyclohexylidene) malononitrile (0.09 mol), 25.7 g of potassium persulfate (0.09 mol) and 2.6 g of water (0.14 mol) were cooled to 0-5° C. Concentrated sulfuric acid was dropwise added to the reaction mixture which was then heated to 70° C. for reaction. After the reaction was completed, the reaction mixture was cooled, poured into ice water and extracted twice with ethyl acetate. The organic phases were combined, dried and crystallized by concentration to give 16.2 g of 2-(3-methylphenyl) malonamide, and the yield was 89%.

Example 6 Preparation of 2-(2,6-diphenyl-4-methylphenyl) malonamide 31.0 g of 2-(2,6-diphenyl-4-methyl-2-ene-1-cyclohexylidene) malononitrile (0.10 mol), 27.0 g of potassium persulfate (0.10 mol) and 2.7 g of water (0.15 mol) were cooled to 0-5° C. Concentrated sulfuric acid was dropwise added to the reaction mixture which was then heated to 70° C. for reaction. After the reaction was completed, the reaction mixture was cooled, poured into ice water and extracted twice with ethyl acetate. The organic phases were combined, dried and crystallized by concentration to give 19.6 g of 2-(2,6-diphenyl-4-methylphenyl) malonamide.

$^1$H NMR (MeOD, 500 MHz): δ 7.50-7.40 (m, 10H), 7.20 (s, 2H), 5.11 (s, 1H), 2.44 (s, 3H).

Example 7 Preparation of Pinoxaden 12.4 g of 2-(2,6-diethyl-4-methylphenyl) malonamide (0.05 mol), 10.5 g of hexahydro-1,4,5-oxadiazepine dihydrochloride (0.06 mol) and 20.2 g of triethylamine (0.20 mol) were stirred and refluxed in xylene for reaction. After the reaction was completed, the reaction mixture was cooled, added with 10.8 g of pivaloyl chloride (0.09 mol) and reacted at room temperature. After the reaction was completed, the reaction mixture was adjusted with dilute hydrochloric acid until pH was acidic and extracted with ethyl acetate. The organic phases were dried and crystallized by concentration to give 14.4 g of Pinoxaden, and the yield was 72%.

$^1$H NMR (CDCl$_3$, 500 MHz, TMS): δ 8.88 (s, 2H), 4.28-4.26 (m, 2H), 3.94-3.93 (m, 2H), 3.89-3.83 (m, 4H), 2.56-2.47 (m, 2H), 2.45-2.40 (m, 2H), 2.39 (s, 3H), 1.12 (t, J=9.0 Hz, 3H), 1.23 (s, 9H).

What is claimed is:

1. A method for preparing 2-aryl malonamide, comprising:
    subjecting compound 1 to an aromatization-hydrolyzation reaction in the presence of an oxidant and water to produce 2-aryl malonamide 2 by one step, as shown in the following reaction scheme:

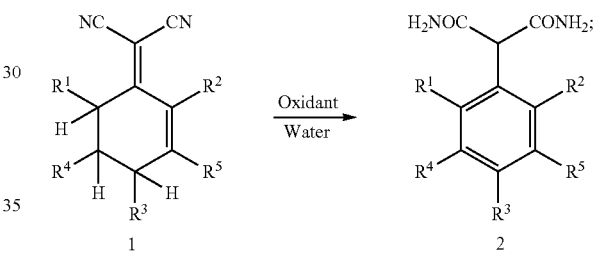

wherein $R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur.

2. The method of claim 1, wherein $R^1$ and $R^2$ each are independently a $C_1$-$C_3$ alkyl group or a $C_6$-$C_{12}$ aryl group; $R^3$ is a $C_1$-$C_3$ alkyl group; and $R^4$ and $R^5$ each are hydrogen.

3. The method of claim 2, wherein $R^1$ and $R^2$ each are ethyl, and $R^3$ is methyl.

4. The method of claim 1, wherein the oxidant is peroxide, oxygen, air or an oxidizing acid; and a molar ratio of the oxidant to the compound 1 is 0.5-2.0:1.

5. The method of claim 4, wherein the oxidant is potassium persulfate or concentrated sulfuric acid; and the molar ratio of the oxidant to the compound 1 is 1.0-1.2:1.

6. The method of claim 1, wherein a temperature of the aromatization-hydrolyzation reaction 0-100° C.

7. The method of claim 6, wherein the temperature of the aromatization-hydrolyzation reaction is 60-80° C.

8. The method of claim 1, wherein the aromatization-hydrolyzation reaction is carried out in the presence of an acid.

9. The method of claim 8, wherein the acid is concentrated sulfuric acid.

10. A method for synthesizing Pinoxaden, comprising:
    1) subjecting compound 1 to an aromatization-hydrolyzation reaction in the presence of an oxidant and water to produce 2-aryl malonamide 2 by one step, as shown in the following reaction scheme:

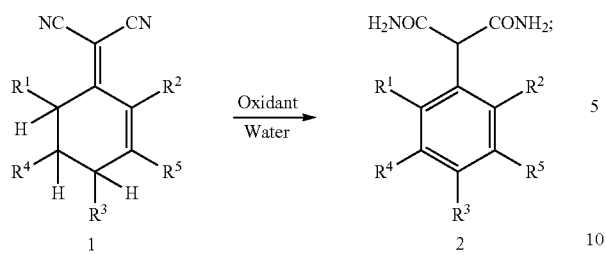
wherein $R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur; and
2) synthesizing Pinoxaden using the 2-aryl malonamide prepared in step 1).
\* \* \* \* \*